US009980804B2

(12) United States Patent
Harris et al.

(10) Patent No.: US 9,980,804 B2
(45) Date of Patent: May 29, 2018

(54) VENA CAVA FILTER WITH FILAMENT

(71) Applicant: C.R. BARD, INC., Murray Hill, NJ (US)

(72) Inventors: Keith S. Harris, Mesa, AZ (US); Andrzej J. Chanduszko, Chandler, AZ (US); Joshua A. Smale, Chandler, AZ (US); Karen A. Diclaudio, Chandler, AZ (US)

(73) Assignee: C. R. BARD, INC., Murray Hill, NJ (US)

( * ) Notice: Subject to any disclaimer, the term of this patent is extended or adjusted under 35 U.S.C. 154(b) by 456 days.

(21) Appl. No.: 14/843,913

(22) Filed: Sep. 2, 2015

(65) Prior Publication Data

US 2015/0374482 A1 Dec. 31, 2015

Related U.S. Application Data

(63) Continuation of application No. 12/093,814, filed as application No. PCT/US2006/044826 on Nov. 17, 2006, now Pat. No. 9,131,999.

(60) Provisional application No. 60/737,895, filed on Nov. 18, 2005.

(51) Int. Cl.
*A61F 2/01* (2006.01)
*A61F 2/07* (2013.01)

(52) U.S. Cl.
CPC ................ *A61F 2/01* (2013.01); *A61F 2/013* (2013.01); *A61F 2/07* (2013.01); *A61F 2002/016* (2013.01); *A61F 2002/018* (2013.01); *A61F 2002/075* (2013.01); *A61F 2210/0004* (2013.01); *A61F 2210/0014* (2013.01); *A61F 2220/0016* (2013.01); *A61F 2230/0006* (2013.01); *A61F 2230/0067* (2013.01); *A61F 2230/0091* (2013.01); *A61F 2250/001* (2013.01)

(58) Field of Classification Search
CPC .... A61F 2/01; A61F 2/013; A61F 2220/0016; A61F 2210/0004; A61F 2210/0014; A61F 2230/0091; A61F 2230/0067; A61F 2230/0006; A61F 2002/018; A61F 2002/016; A61F 2250/001; A61F 2002/075; A61F 2/07
See application file for complete search history.

(56) References Cited

U.S. PATENT DOCUMENTS 5,669,933 A * 9/1997 Simon ...................... A61F 2/01 600/191
5,709,704 A * 1/1998 Nott ......................... A61F 2/01 606/191

(Continued)

*Primary Examiner* — Katherine M Shi
*Assistant Examiner* — Michael Mendoza
(74) *Attorney, Agent, or Firm* — Garvey, Smith & Nehrbass, Patent Attorneys, LLC; Seth M. Nehrbass; Julie R. Chauvin

(57) ABSTRACT

A vena cava filter is described, having one or more frame members or an elongated member arranged in helical fashion. A plurality of filaments connect frame members or portions of the elongated member. The filaments may be made of suture material. Hooks may be placed on a free end of the filaments, along the length thereof, or on one or more frame members to engage the blood vessel wall and anchor the filter. A retrieval member may be positioned on the filter to facilitate withdrawal of the filter from the blood vessel.

18 Claims, 4 Drawing Sheets

20 22 23 24 26

(56) References Cited

U.S. PATENT DOCUMENTS

| | | | | |
|---|---|---|---|---|
| 6,214,025 | B1 * | 4/2001 | Thistle | A61F 2/01 606/200 |
| 6,267,776 | B1 * | 7/2001 | O'Connell | A61F 2/01 606/158 |
| 6,682,540 | B1 * | 1/2004 | Sancoff | A61B 17/0644 606/153 |
| 8,267,954 | B2 * | 9/2012 | Decant, Jr. | A61B 5/02007 606/200 |
| 2001/0044634 | A1 * | 11/2001 | Don Michael | A61F 2/013 606/200 |
| 2010/0043197 | A1 * | 2/2010 | Abbate | A61F 2/95 29/505 |
| 2010/0168786 | A1 * | 7/2010 | Dower | A61F 2/013 606/200 |

* cited by examiner

10
D12
L
12

D13
13
16
D14
14
18
20
22
23
24
26

27
22
28
24
23
21
29

27
22
25
28
24
23
21
29

27
22
28
25
24
23
21
29

VENA CAVA FILTER WITH FILAMENT

PRIORITY

This application is a continuation of U.S. patent application Ser. No. 12/093,814 filed Jun. 8, 2009, now U.S. Pat. No. 9,131,999, which is a U.S. national stage application under 35 USC § 371 of International Application No. PCT/US2006/044826, filed Nov. 17, 2006, which claims the benefit of priority to U.S. Application No. 60/737,895, filed Nov. 18, 2005, each of which is incorporated by reference in its entirety into this application.

BACKGROUND

Inferior vena cava (IVC) filters are devices configured for insertion into the inferior vena cava to capture particles that may be present in the blood stream which, if transported to, for example, the lungs could result in serious complications and even death. Typically, IVC filters are utilized in patients who have a contraindication to anticoagulation or in patients developing clinically apparent deep vein thrombosis (DVT) and/or pulmonary embolism (PE). Patients who have recently suffered from trauma, have experienced a heart attack (myocardial infarction), or who have undergone major surgical procedure (e.g., surgical repair of a fractured hip, etc.) may develop clinically apparent DVT. When a thrombus clot loosens from the site of formation and travels to the lung, it may cause PE, a life-threatening condition. An IVC filter may be placed in the circulatory system to intercept one or more clots and prevent them from entering the lungs. IVC filters are either permanent or retrievable.

There are many different configurations for IVC filters, including those that include a central hub from which extend a plurality of struts that form filter baskets having a conical configuration, such as disclosed in U.S. Pat. No. 6,258,026, which is incorporated by reference in its entirety into this application. Other IVC filter configurations utilize wires and/or frame members to form straining devices that permit flow of blood while trapping larger particles. IVC filters are generally configured for compression into a small size to facilitate delivery into the inferior vena cava and subsequent expansion into contact with the inner wall thereof. The IVC filter may later be retrieved from the deployed site by compressing the legs, frame members, etc., depending on the filter configuration. Typically, an IVC filter will include hooks or anchoring members for anchoring the filter in position within the inferior vena cava. The hooks may be more elastic than the legs or frame members to permit the hooks to straighten in response to withdrawal forces, which facilitate withdrawal from the endothelium layer of the blood vessel without risk of significant injury to the vessel wall.

Applicants have recognized that it would be desirable to provide an IVC filter that incorporates one or more filaments, such that the filament(s) provide a framing function and/or a filtering function, in order to provide advantageous properties to the IVC filter. Embodiments of such IVC filters are described herein.

BRIEF SUMMARY OF THE INVENTION

Accordingly, IVC filters with one or more filaments are described herein. In one embodiment, a blood vessel filter includes two or more generally arcuate frame members spaced apart and arranged along a longitudinal axis that extends through the two or more frame members, and a plurality of filaments connecting the frame members. The frame members may include a first section and a second section, the first section having a portion disposed inside the second section. In another embodiment, a blood vessel filter includes an elongated member arranged in a helical radially expanding path about and along a longitudinal axis, and a plurality of filaments connected to the member.

In yet another embodiment, an implantable medical device includes a continuous generally circular member defining a frame having an open interior portion, and a plurality of filaments attached to the frame, each filament having a first end connected to the frame at a first point and a second opposite end connected to the frame at a second point different from the first point, the filaments together defining a generally planar mesh-like surface spanning the interior portion of the frame. In another embodiment, an implantable medical device includes a support structure having an open proximal end, and one or more filaments attached to the frame to define a generally planar mesh-like surface spanning the open proximal end.

These and other embodiments, features and advantages will become more apparent to those skilled in the art when taken with reference to the following more detailed description of the invention in conjunction with the accompanying drawings that are first briefly described.

DETAILED DESCRIPTION OF THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The filter embodiments discussed below may be used for insertion into the inferior vena cava or other blood vessels or cavities in a mammalian body. As used herein, the term "suture material" means a material that is, or could be, used as a suture thread by a surgeon, including, for example, synthetic polymers, polyglycolic acid (PGA), polydioxanone (PDS), polyglactin, nylon, polypropylene (prolene), silk, catgut, non-absorbable/non-biodegradable materials, and combinations thereof Included in the term "suture material" are both monofilament and multifilament arrangements. Also, as used herein, the term "hook" means a member configured to engage a blood vessel wall which may include, for example, the hooks shown and described in U.S. Pat. No. 6,258,026, which is incorporated by reference in its entirety into this application.

Figures 1, 2A:
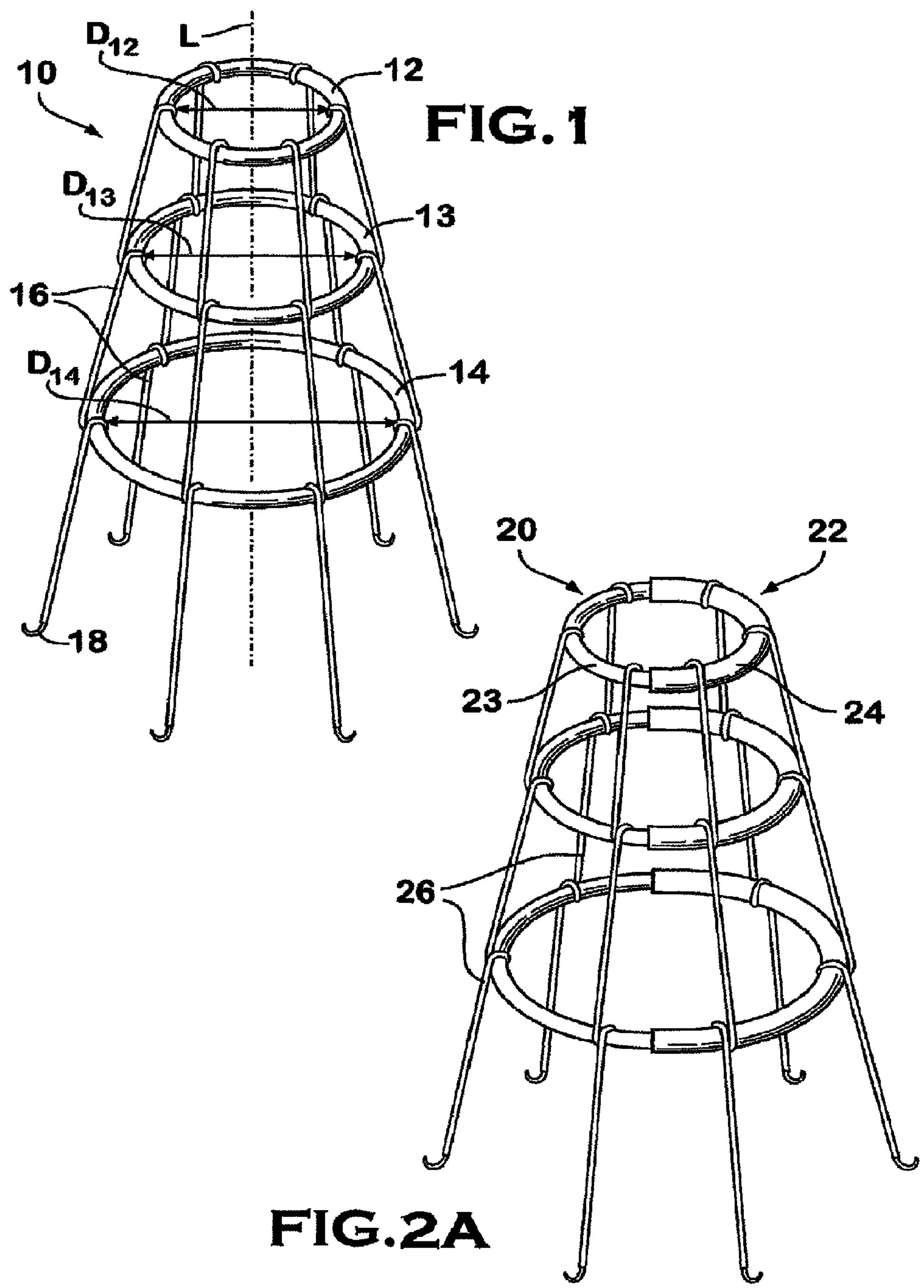
FIG. 1 is a side perspective view of one embodiment of a filter with frame members.
FIG. 2A is a side perspective view of another embodiment of a filter with frame members that are adjustable.

Referring to FIG. 1, one embodiment of a filter is illustrated. Filter 10 includes two or more generally arcuate frame members that are spaced apart and arranged along a longitudinal axis L that extends through two or more frame members. In the embodiment shown, frame member 12 is positioned at a proximal end of filter 10 and frame member 13 is spaced apart from frame member 12 along a longitudinal axis L of the filter. Spaced apart from frame member 13 along longitudinal axis L is frame member 14. The frame members 12, 13, 14 have a generally arcuate shape, which in some embodiments may be circular, elliptical, etc., and which increase in size in the distal direction such that the diameter D12 of frame member 12 is less than the diameter D13 of frame member 13, and the diameter D13 of frame member 13 is less than the diameter D14 of frame member 14. In another embodiment, the diameters of all the frame members are substantially equivalent, while in another embodiment only some of the frame members have diameters that are substantially equivalent. In one embodiment, the frame members decrease in diameter from a proximal end of the filter to a mid-region of the filter and then increase in diameter from the mid-region of the filter to a distal end of the filter. Other embodiments with respect to the shapes and sizes of the frame members in view of the examples provided are also possible and are within the scope of the invention, as one skilled in the art would appreciate. The frame members 12, 13, 14 of filter 10 are shown in an expanded configuration, defining an expanded perimeter of the filter 10. For delivery of the filter 10 to a blood vessel, the frame members 12, 13, 14 are compressed to a collapsed configuration. The frame members 12, 13, 14 in the collapsed configuration define a collapsed perimeter of the filter 10 smaller than the expanded perimeter of the filter 10.

The frame members (or filaments) may be made of any material typically used for implantable medical devices as known to one skilled in the art, such as, for example, stainless steel, shape memory metals, shape memory alloys, super elastic shape memory metal alloys, metal alloys, shape memory polymers, polymers, and combinations thereof. The frame members may also be made of a bio-resorbable material such as, for example, the materials shown and described in U.S. Pat. No. 6,287,332; and U.S. Patent Application Publication No. 2002/0004060, which are incorporated by reference in their entireties into this application.

The generally arcuate frame members 12, 13, 14 of filter 10 are connected together via a plurality of filaments 16. In one embodiment, the filaments 16 include suture material, although in other embodiments, the filaments may include materials discussed above with respect to the frame members. The filaments 16 are attached to each frame member along the longitudinal axis L, as shown in filter 10. However, in other embodiments, the filaments can be attached to every odd frame member along the longitudinal axis L (i.e., the most proximal frame member, the third frame member counting from the proximal frame member, the fifth frame member, etc.), or every even frame member along the longitudinal axis L, or every third frame member along the longitudinal axis L, etc. In other embodiments, one filament is attached to each frame member of the filter along the longitudinal axis L, while an adjacent filament is attached to every odd frame member, or every even frame member, or every third frame member, etc. In still other embodiments, one or more filaments could be attached to every odd frame member or every even member along the longitudinal axis L, while the remainder of the filaments are attached to each frame member along the longitudinal axis L. Certainly other embodiments not specifically mentioned are also within the scope of the invention with respect to attachment of filaments to frame members.

The filaments 16 are attached to the frame members 12, 13, 14 in filter 10 by wrapping the filament one time around each frame member. However, other possibilities for attaching the filaments to the frame members include wrapping the filament multiple times around the frame member, tying the filament to the frame member or members, heating the filament adjacent to the frame member to create a bond therebetween, applying an adhesive to the filament and/or the frame member, applying a solvent to the filament and/or frame member, etc. Of course, other possibilities for attaching a filament to frame members known to one skilled in the art are also within the scope of this invention.

The filaments 16 of filter 10 extend beyond the most distal frame member 14, having a free end attached to a hook 18. The hook 18 can have many different configurations as known to one skilled in the art, such as, for example, the hooks disclosed in U.S. Pat. No. 6,258,026. While each of the filaments 16 of filter 10 are shown with a hook attached to a free end, in other embodiments one or more filaments may terminate at the most distal frame member without a free end, while other filaments extend beyond the most distal frame member, having a free end with a hook attached. In other embodiments (see FIG. 2), none of the filaments extend beyond the most distal frame member, in which case the hook 18 may be attached to the frame member or to the filament at some point along its length. The hook 18 is configured for engaging the wall of the blood vessel into which the filter 10 is deployed and may be made of any material discussed above with respect to the frame members. In one embodiment, the hook contains a linear portion connected to an arcuate portion that terminates in a point, as shown and described in U.S. Pat. No. 6,258,026. In one embodiment, the arcuate member has a cross-sectional area smaller than the cross-sectional area of the linear portion, as shown and described in U.S. Pat. No. 6,258,026. In the preferred embodiments, each of the hooks has a largest diameter on its arcuate portion of less than about 0.013 inches, preferably about 0.0085 inches and most preferably 0.0105 inches. Details of the hooks are shown and described in U.S. patent application Ser. No. 11/429,975, filed May 9, 2006, which application is incorporated by reference in its entirety into this application. Alternatively, the hooks can be those shown and described in U.S. Patent Application Publication Nos. 2005/0101982 and 2005/0131451, which are incorporated by reference in their entireties into this application.

FIG. 2A shows another embodiment of a filter 20. Filter 20 is similar to filter 10 in that it contains three frame members 22 connected together by filaments 26, which in one embodiment are made of suture material, and in other embodiments are made of materials discussed above in connection with possible materials for the frame members. The filaments 26 of filter 20 do not have a free end extending beyond the most distal frame member. Thus, while in some embodiments, the filaments may include a free end with a hook as described above, in other embodiments, a hook or hooks may be attached along the circumference of one or more frame members or may be attached to one or more filaments along their length. Other embodiments include hooks on both a free end of the filament(s) and the frame member and/or along the length of the filament(s). The frame members 22 are shown in this embodiment in a configuration in which the size of the frame members 22 increase in diameter from a proximal end to a distal end along a longitudinal axis. The frame members 22, however, in filter 20 are unique in that the frame member 22 are adjustable.

Specifically, frame members 22 include a first section 23 and a second section 24, the first section 23 having a portion disposed inside and slidable within the second section 24. Thus, the size and shape of the frame members 22 may be adjusted by moving the first section 23 with respect to the second section 24. A limit member to prevent separation may be included on either or both the first section 23 and the second section 24. In one embodiment, shown in FIG. 2B, a limit member is in the form of a ring 28 coupled, connected to or molded onto the first section 23 of the frame member 22 about the portions that are disposed within the second section 24. In this embodiment, the second section 24 of the frame member 22 contains a shoulder 27 positioned in a passage 21 of the second section 24 adjacent both openings 29 through which portions of the first section 23 are positioned. The shoulders 27 are configured to prevent passage of the rings 28 out of the openings 29, thereby preventing separation of the first section 23 from the second section 24. The rings 28 may be positioned anywhere along the length of the first section 23 and may be sized to provide a friction fit with the passage 21 of second section 24 in order to prevent the first section 23 from movement with respect to second section in the absence of a clinically significant force. Also, the passage 21 could contain two additional shoulders within the passage 21 and on opposite sides of the rings 28 to prevent movement within the passage 21, thereby providing a predetermined constraint on the size and shape of the frame member 22. Of course, there are numerous possibilities for the limit member as understood by one skilled in the art.

For insertion into a blood vessel, the frame members 22 are placed in a collapsed configuration by moving a portion of the first section 23 into the second section 24. In the collapsed configuration, the frame members 22 define a first outer perimeter. Once inserted and positioned within the blood vessel, the frame members 22 are placed in an expanded configuration by moving a portion of the first section 23 that was previously inside the second section 24 out of second section 24. The frame members 22 in the expanded configuration define a second outer perimeter greater than the first outer perimeter. Movement of a portion of the first section 23 out of the second section 24 to place the frame members 22 in an expanded configuration may be accomplished by methods known to one skilled in the art, such as, for example, applying pressure to an interior surface of the frame members using a balloon catheter.

Figure 2B:
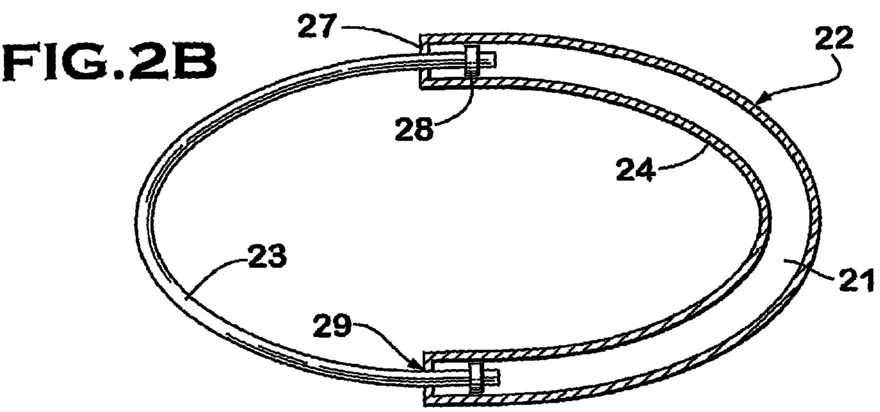
FIG. 2B is a cut-away view of one embodiment of a frame member of FIG. 2A.
Figure 2C:
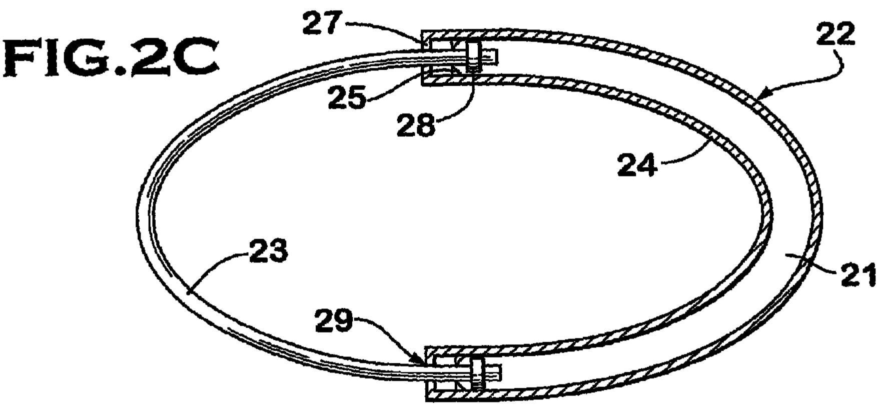
FIG. 2C is a cut-away view of another embodiment of a frame member of FIG. 2A, shown in a collapsed configuration.
Figure 2D:
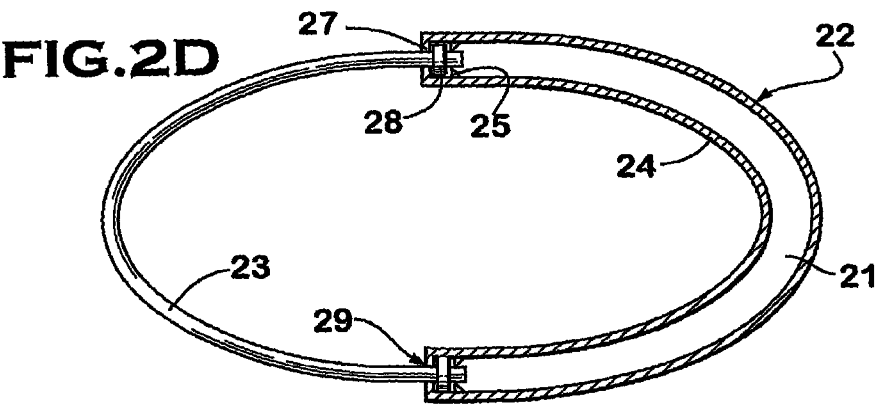
FIG. 2D is a cut-away view of the embodiment of a frame member of FIG. 2C, shown in an expanded configuration.

Referring now to FIGS. 2C and 2D, another embodiment for the frame members 22 is illustrated. In this embodiment, the first section 23 can be locked with respect to second section 24 following delivery into a blood vessel. As with the embodiment of FIG. 2A, first section 23 includes limit members 28 that are positioned within passage 21 of second section 24. Second section 24 contains shoulders 27, as in FIG. 2A, but also contains tab members 25 that impart a locking function to the frame members 22. Specifically, FIG. 2C illustrates the frame member 22 in a collapsed configuration for delivery into a blood vessel, such as the inferior vena cava, with limit members 28 positioned within passage 21 distant from the openings 29. After the filter has been positioned in the blood vessel, the frame member 22 is placed in an expanded configuration following deployment thereof as described above, which is shown in FIG. 2D.

As the frame member 22 is expanded, the first section 23 has portions within the second section 24 that are moved out of the second section 24. As these portions of first section 23 are moved with respect to second section 24, the limit members 28 are moved in a direction toward the openings 29. Tab members 25 are flexible such that as limit members 28 contact the tab members 25, the tab members 25 flex in a direction toward the openings 29, permitting the limit members 28 to move toward the openings. After the limit members 28 move past the tab members 25 such that they are no longer in contact therewith, the tab members 25 resiliently move back into their un-flexed position, thereby preventing movement of the limit members 28 away from the openings 29, as shown in FIG. 2D. Due to the presence of the shoulders 27 on the second section 24, the limit members 28 are also prevented from movement out of the openings. Thus, the first section 23 is locked into position with respect to the second section 24. The tab members 25 may be configured to permit one-way movement (such that the first section 23 is permanently locked with respect to the second section 24) or two-way movement (such that the frame member 22 is collapsible to permit removal from the blood vessel), depending on whether the filter is intended to be permanent or temporary. The frame member 23 can be made of a suitable material such as, for example, shape memory alloy, shape memory polymer, super elastic shape memory metal alloy, linear elastic shape memory metal alloy. Alternatively, a biasing element can be provided in the internal space 21 to bias the section 23 towards a deployed configuration. Preferably, at least the frame member 23 is made of Nitinol so that the frame member 23 self-expand into a larger configuration when placed in a suitably warm environment.

Figure 3:
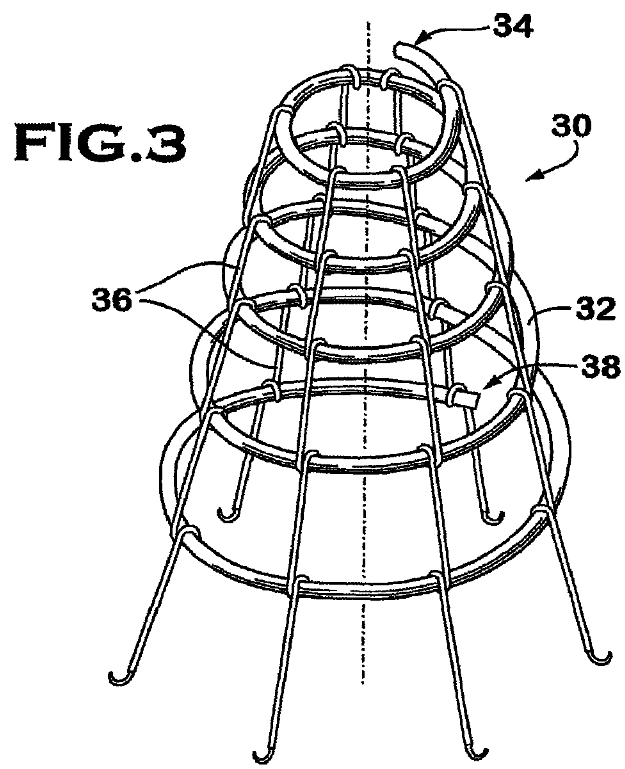
FIG. 3 is a side perspective view of an embodiment of a filter with an elongated member.

FIG. 3 illustrates another embodiment of a filter 30. Filter 30 includes an elongated member 32 arranged in a helical radially expanding path about and along a longitudinal axis L from a proximal end 34 to a distal end 38, the elongated member 32 having a free end at both the proximal end 34 and distal end 38. The elongated member 32 may be made of any material discussed above with respect to the frame members of FIG. 1. As shown, each of the filaments 36 are attached to the elongated member 32 at points along each turn or successive winding of the helical path, although, as discussed above in reference to FIG. 1, numerous possibilities exist for the attachment points of the filaments. For example, select filaments could be attached to every odd turn along the helical path (i.e., counting the first turn as 1 and proceeding therealong), or every even turn along the helical path, etc. As discussed above, the method of attachment of the filaments 36 to the elongated member 32 can include use of adhesives, solvents, wrapping of the filament around the elongated member, tying the filament to the elongated member, etc.

Also, it should be appreciated for all embodiments described herein that filaments could be attached only to adjacent frame members or helical turns, rather than extending down the length of the filter. Thus, for example, referring to FIG. 3, a first set of filaments 36 could be attached only to the first helical turn and second helical turn, while a second set of filaments 36 could be attached only to the second helical turn and the third helical turn. Alternatively, select filaments could extend down the length of the filter 30, attached to each helical turn, while other filaments are attached only to consecutive turns, or every odd turn, or every even turn, etc. As with the filters 10 and 20, the filaments 36 of filter 30 may extend beyond the distal end 38 having a free end to which a hook is attached. Alternatively, or in addition to the preceding, hooks may be attached to the elongated member 32 along its length and/or to the filaments along their length as would be appreciated by one skilled in the art. As with all embodiments described herein (and those within the scope of the invention not specifically described), the filaments may include a suture material or any of those materials discussed as possibilities for the frame members of FIG. 1.

Figure 4:
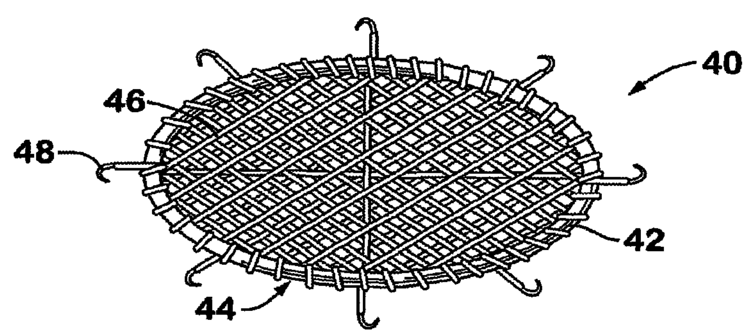
FIG. 4 is a perspective view of another embodiment of a filter with a frame member having an open interior portion spanned by a generally planar mesh-like surface.

Referring now to FIG. 4, another embodiment of a filter 40 is illustrated. Filter 40 includes a frame member 42 that is shown as continuous and generally circular, having an interior portion that is open. The frame member 42 can be made of any material discussed above with respect to the frame members of FIG. 1. Attached to the frame member 42 are filaments 46 that span the open interior portion such that a first end of each filament is attached to the frame at a first point and a second end of each filament is attached to a second point different from the first point, creating a generally planar mesh-like surface 46 as shown in FIG. 4. In one embodiment the attachment points for each filament 46 are spaced approximately equidistant to provide a uniform mesh-like surface 46. The filaments 46 may include a suture material or any of those materials discussed as possibilities for the frame members of FIG. 1. Attached to a surface of the frame member 42 are hooks 48, which can be configured as discussed above and made of materials such as those discussed as possibilities for the frame members of FIG. 1. The mesh-like surface can be provided with a suitable open area ratio such that blood cells can pass through the mesh-like surface and the pressure drop across the mesh-like surface is generally insignificant. In the preferred embodiments, the open area ratio is at least 10:1 and the pressure drop is less than 0.2 inch of Hg (as simulated in a 28 mm internal pipe diameter with fluid that simulates blood flow).

The filter 40 can be configured in a first configuration smaller than the configuration shown in FIG. 4. For example, the filter 40 can be twisted into a figure-8 and bent at the mid-point of the figure-8 into a smaller generally circular configuration and loaded into a suitable delivery catheter. Preferably, the filter 40 is sized and loaded into a ?French internal diameter delivery catheter. Applicant has recognized that this embodiment provides for an advantage not heretofore available in that the filter 40 can be delivered either from the jugular vessel or femoral vessel without regard to the orientation of the filter 40.

Figure 5A:
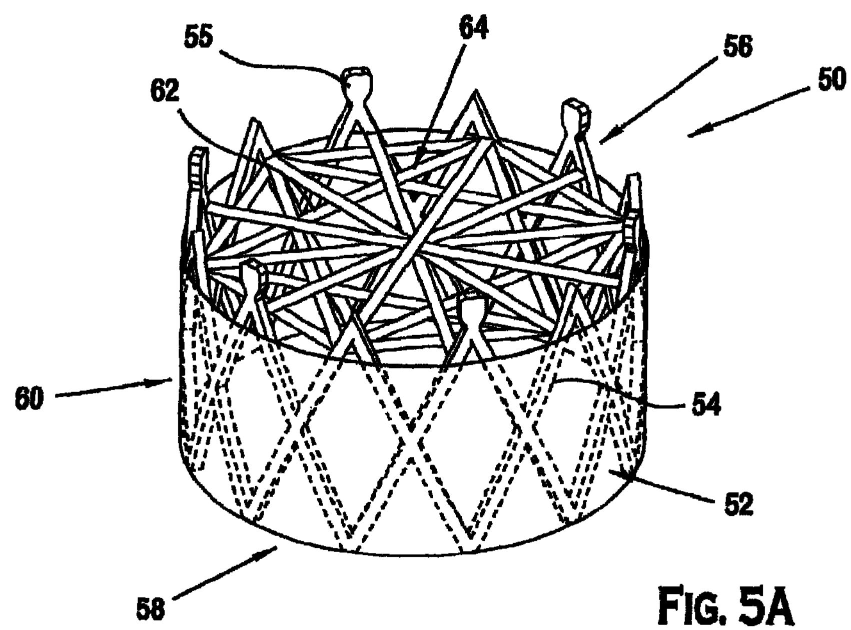
FIG. 5A is a perspective side view of another embodiment of a filter with a support structure having an open proximal end spanned by a generally planar mesh-like surface.

Referring to FIG. 5A, another embodiment of a filter 50 is illustrated. Filter 50 includes a support structure 52, which in a preferred embodiment is a stent. In one embodiment, the support structure 52 is a ring stent with anchors as described in U.S. Patent Application Publication No. 2003/0158595, which is incorporated by reference in its entirety into this application. In one embodiment, the support structure 52 includes a cylindrical shape with a generally uniform distribution of struts 54. The struts 54 together form repeating diamond shapes around the circumference of the structure 52 with a proximal end 56 and a distal end 58. The support structure may include hooks, which can be configured as discussed above and made of materials such as those discussed as possibilities for the frame members of FIG. 1, on the proximal end 56 and/or distal end 58. In addition, markers 55 may optionally be included on one or both of the proximal and distal ends 56, 58, such as the marker elements described in U.S. Patent Application Publication No. 2004/0015228, which is incorporated by reference in its entirety into this application. The markers 55 preferably include a radiopaque material, such as, for example, tantalum, platinum, gold, iridium or a combination thereof. The markers 55 can be attached to the support structure using methods known to one skilled in the art (e.g., laser welding) and can be arranged in a uniform pattern (e.g., every other strut end, every third strut end, etc.) or a non-uniform pattern. In one embodiment, only a single marker 55 is attached to the proximal end 56 of the support structure 52.

In one embodiment, the filter 50 includes a covering material 60, such as a graft member, positioned on an inner surface of the support structure 52, an outer surface of the support structure 52, or both. The covering material 60 may include a biocompatible material, such as, for example, expanded polytetrafluoroethylene (ePTFE), polyester, polyurethane, fluoropolymers, such as perfouorelastomers and the like, polytetrafluoroethylene, silicones, urethanes, and combinations thereof, but in a preferred embodiment the covering material 60 includes ePTFE. In one embodiment, the covering material 60 includes an inner ePTFE graft 62 and an outer ePTFE graft 64 that are fused together through openings between struts 54 to at least partially encapsulate the support structure 52. In the embodiment shown in FIG. 5A, the proximal end surfaces of the support structure 52 are left uncovered by the covering material 60, in order, for example, to provide a platform for markers, hooks or both, and/or to provide an attachment point for one or more filaments 62.

The filament or filaments 62 are attached to the support structure 52, spanning an open region at the proximal end 56 of the support structure 52, to provide a mesh-like surface 64 configured to prevent the passage of blood clots or other debris entering through the open distal end 58 of the support structure 52. In one embodiment, windings of a single filament or filaments 62 are positioned such that a first end of each winding or filament 62 is attached to the support structure 52 at a first point and a second end of each winding or filament 62 is attached to a second point different from the first point, creating a generally planar mesh-like surface 64. In one embodiment, the attachment points for each winding or filament 62 are spaced approximately equidistant to provide a uniform mesh-like surface 64. In another embodiment, the filament or filaments 62 are twisted together, wrapped around adjacent struts on the support structure, or are otherwise arranged in a non-uniform manner to provide a non-uniform mesh-like surface 64. The filament or filaments 62 may be attached to the support structure prior to or following the disposition of the covering material 60 in embodiments including a covering material 60. In addition to spanning the open proximal end 56, the filament or filaments 62 may be disposed transverse to the mesh-like surface 64, extending between the proximal end 56 and the distal end 58. Alternatively, the filament or filaments 62 may be attached only to the proximal end 56 of the support structure 52 (e.g., portions extending proximal of the covering material 60).

Figure 5B:
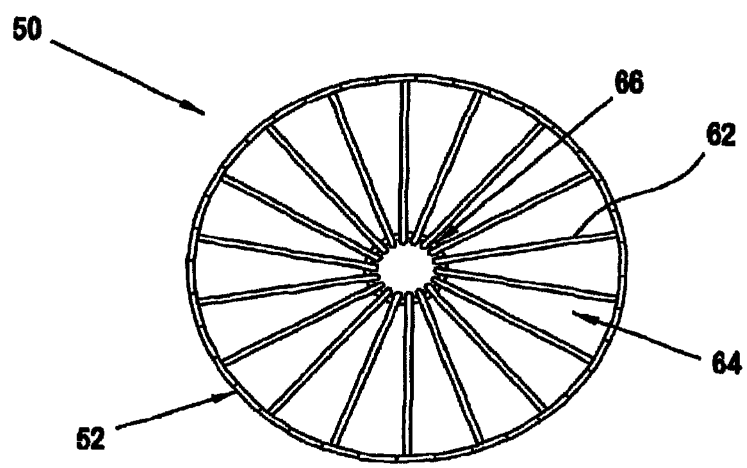
FIG. 5B is a top view of a variation of the embodiment of FIG. 5A.

FIG. 5B is a top perspective view of alternate embodiment of the filter 50 that includes a ring 66 to which the filament or filaments 62 are attached (e.g., by winding around, etc.)

or that is created through the weaving of one or more filaments 62. The ring 66 facilitates passage of a guidewire and can be utilized as a platform for attaching a retrieval member. In embodiments including a ring 66 made of a metal or polymer material, for example, a retrieval member could be configured for temporary attachment to the ring 66. The filter 50 is generally collapsible from an expanded configuration with an expanded perimeter as shown in FIGS. 5A and 5B to a collapsed configuration with a collapsed perimeter smaller than the expanded perimeter (not shown). In one embodiment, the filter 50 is collapsed to the collapsed configuration by applying a force to the mesh-like surface 64 in a direction away from the filter 50. In one embodiment, a retrieval member is attached to the mesh-like surface 64 and pulled so that the force applied to the surface 64 is generally uniformly distributed. The retrieval member may be permanently attached to the filament or filaments 62 forming the mesh-like surface 64 or may be temporarily attached thereto for retrieval of the filter 50 from a deployed position in a blood vessel. In one embodiment, the retrieval member is attached (permanently or temporarily) to the support structure 52.

As with the embodiment described above in connection with FIG. 4, the mesh-like surface 64 can be provided with a suitable open area ratio such that blood cells can pass through the mesh-like surface 64 and the pressure drop across the mesh-like surface 64 is generally insignificant. In the preferred embodiments, the open area ratio is at least 10:1 and the pressure drop is less than 0.2 inch of Hg (as simulated in a 28 mm internal pipe diameter with fluid that simulates blood flow).

Delivery of various embodiments of the filter described herein can be by any suitable techniques. For example, the filter can be actively delivered via a spring force provided in a delivery catheter. A coil spring can be coupled to a pusher member disposed in the lumen of the delivery catheter. The coil spring is compressed prior to delivery. Once actuated, the spring provides an abrupt kinetic force to the filter to eject the filter out of the delivery catheter. Alternatively, other motive force such as a pressurized liquid can be used to eject (via an intermediate member such as a pusher in the lumen of the delivery catheter) the filter out of the delivery catheter. Additionally, a balloon can also be used to ensure full radial expansion of each filter.

Each of the embodiments described herein may also include a retrieval member to facilitate retrieval of the filter from the blood vessel in which it is placed. The retrieval member may be configured as a hook, loop, rod, shaft, etc., which cooperates with a removal device to permit removal of the filter from the blood vessel. One example of a retrieval member is disclosed in U.S. Pat. No. 6,156,055, which is incorporated by reference in its entirety into this application. The retrieval member may be placed on the most proximal frame members (FIGS. 1-2), at the proximal end 34 of the elongated member 32 (FIG. 3), or along a surface of the frame member 42 (FIG. 4). Alternatively, the retrieval member may be positioned along the length of a filament in any of the embodiments described herein, or on a more distal section of the filter (e.g., frame member 13 of FIG. 1, along the length of the elongated member 32 of FIG. 3, etc.).

Each of the embodiments described herein can be utilized for a blood vessel of at least 28 millimeters. Moreover, each of the embodiments described herein can be loaded into a delivery catheter having an inside diameter of less than about 10 French. The length of each embodiment, when deployed, can be about 50 millimeters or less.

Where the filter is to be utilized with bio-active agents to control the formation of emboli, bio-active agents can be coated to a portion or the entirety of the filter for controlled release of the agents once the filter is implanted. The bio-active agents can include, but are not limited to, vasodilator, anti-coagulants, such as, for example, warfarin and heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) Ifb/IIIa2 inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothio glucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A blood vessel filter comprising:

two or more generally arcuate frame members spaced apart and arranged along a longitudinal axis of the filter;

and a plurality of filaments connecting the frame members; wherein the frame members have a circular configuration; and wherein each of the frame members comprises a first section that has at least one portion slidably disposed inside a second section in a first configuration of the filter, and wherein the at least one portion is slidably disposed outside the second section in a second configuration of the filter.

2. The filter of claim 1 wherein at least one of the frame members and filaments comprise suture material.

3. The filter of claim 1 wherein each of the filaments loop at least one time around each of the frame members along the longitudinal axis.

4. The filter of claim 1 wherein at least some of the filaments include a hook that engages a wall of a blood vessel.

5. The filter of claim 4 wherein the hooks lay on a free end of the filaments.

6. The filter of claim 1 wherein each frame member has a first diameter and a second diameter, and at least the first diameter of successive members increases along the longitudinal axis.

7. The filter of claim 6 wherein each frame member comprises a continuous member.

8. The filter of claim 7 wherein the shape memory material is one of shape memory alloy, shape memory polymer, super elastic shape memory metal alloy, linear elastic shape memory alloy, or combinations of these.

9. The filter of claim 8 wherein the continuous member comprises a shape memory material.

10. The filter of claim 8 wherein at least one of the frame members comprises a bioabsorbable material.

11. The filter of claim 10 wherein at least one of the frame members includes at least one hook.

12. The filter of claim 11 wherein the at least one hook comprises a linear portion connected to an arcuate portion that terminates in a point, the arcuate member having a cross-sectional area smaller than the cross-sectional area of the linear portion.

13. The blood vessel filter of claim 1 further comprising a hook or barb positioned on one or more of the filaments.

14. The blood vessel filter of claim 13 wherein the first configuration defines a first outer perimeter smaller than a second outer perimeter of the second configuration.

15. The blood vessel filter of claim 14 wherein one of the first portion and second portion comprises a limit member to prevent separation of the first section from the second section.

16. The blood vessel filter of claim 14 wherein one of the first portion and second portion comprises a lock to prevent further adjustment of the first section relative to the second section.

17. The blood vessel filter of claim 15 wherein at least one of the frame members comprises a bioabsorbable material.

18. The blood vessel filter of claim 15 further comprising at least one hook disposed on at least one of the frame members.

* * * * *